United States Patent
Melchor

(10) Patent No.: US 12,207,857 B2
(45) Date of Patent: Jan. 28, 2025

(54) RATCHET ROD BENDER AND RELATED METHODS

(71) Applicant: Medos International Sarl, Le Locle (CH)

(72) Inventor: Jonathan Melchor, Providence, RI (US)

(73) Assignee: Medos International Sàrl, Le Locle (CH)

( * ) Notice: Subject to any disclaimer, the term of this patent is extended or adjusted under 35 U.S.C. 154(b) by 829 days.

(21) Appl. No.: 17/341,851

(22) Filed: Jun. 8, 2021

(65) Prior Publication Data

US 2022/0387089 A1    Dec. 8, 2022

(51) Int. Cl.
| | |
|---|---|
| A61B 17/88 | (2006.01) |
| A61B 17/70 | (2006.01) |
| A61B 90/00 | (2016.01) |
| A61B 17/00 | (2006.01) |

(52) U.S. Cl.
CPC ...... *A61B 17/8863* (2013.01); *A61B 17/7013* (2013.01); *A61B 17/7074* (2013.01); *A61B 90/03* (2016.02); *A61B 2017/00407* (2013.01); *A61B 2090/033* (2016.02)

(58) Field of Classification Search
CPC .............. A61B 17/8861; A61B 17/8863; B21D 7/024; B21F 1/002
USPC ..................................................... 606/101
See application file for complete search history.

(56) References Cited

U.S. PATENT DOCUMENTS

| | | |
|---|---|---|
| 4,474,046 A | 10/1984 | Cook |
| 5,819,580 A | 10/1998 | Gauthier |
| 6,006,581 A | 12/1999 | Holmes |
| 8,491,601 B2 | 7/2013 | Schmuck et al. |
| 9,003,859 B2 | 4/2015 | Paris et al. |
| 9,186,195 B2 | 11/2015 | Petit et al. |
| 9,421,596 B2 | 8/2016 | Paris et al. |
| 9,718,108 B2 * | 8/2017 | Latoria .............. B21D 11/12 |
| 9,839,463 B2 | 12/2017 | Dominik et al. |
| 9,872,716 B2 | 1/2018 | Cordaro et al. |

(Continued)

FOREIGN PATENT DOCUMENTS

| | | |
|---|---|---|
| WO | 2012062464 A1 | 5/2012 |
| WO | 2017020152 A1 | 2/2017 |
| WO | 2020221710 A1 | 11/2020 |

OTHER PUBLICATIONS

International Search Report and Written Opinion issued for Application No. PCT/EP2022/065345, dated Aug. 16, 2022 (11 pages).

*Primary Examiner* — Eduardo C Robert
*Assistant Examiner* — Christina Negrellirodriguez
(74) *Attorney, Agent, or Firm* — Barnes & Thornburg LLP

(57) ABSTRACT

Implant bending instruments disclosed herein can have a plurality of bending elements that can be symmetrically driven to bend or contour an implant, such as a spinal rod. A single actuator handle can be moved to drive a compound gear train and move the bending elements to intersect an implant-receiving channel and bend an implant received therein. Instruments of the present disclosure can have an increased mechanical advantage than conventional bending instruments thereby allowing for an increased amount of force to bend an implant. A locking pawl can selectively prevent counter rotation of the gear train such that the handle can be actuated a plurality of times to achieve a desired contour angle.

23 Claims, 10 Drawing Sheets

(56) References Cited

U.S. PATENT DOCUMENTS

| | | |
|---|---|---|
| 10,327,828 B2 | 6/2019 | Rinner |
| 10,702,323 B2 | 7/2020 | Richards et al. |
| 10,786,287 B2 | 9/2020 | Beger et al. |
| 2015/0298192 A1* | 10/2015 | Paris ................ B21F 1/002 |
| | | 72/372 |
| 2016/0089195 A1 | 3/2016 | Cordaro et al. |
| 2017/0042597 A1 | 2/2017 | Rinner |

* cited by examiner

RATCHET ROD BENDER AND RELATED METHODS

FIELD

Devices and methods for bending an implant, e.g., a spinal rod, are disclosed herein.

BACKGROUND

Implants can be used in orthopedic surgery to stabilize, support, or correct anatomy. In spinal surgery, for example, a spinal rod implant, along with other hardware, can provide stability to the spine and, in cases of deformity, can be utilized to correct the shape of the spine. Often times the spinal rod, or other implant, must be shaped to accommodate the particular needs of a patient or surgical procedure. For example, a spinal rod can be contoured to match a desired template shape tailored to patient-specific anatomy by bending the rod.

The force required to bend or otherwise shape a spinal rod can be based, at least in part, on material composition and size of the rod. With advances in implant technology, new materials can be used to form spinal rods that may improve strength and durability of the implant. These new materials, however, can require greater force and displacement to bend than can be provided by conventional rod benders. For example, prior surgeon-operated "French" rod benders utilize three points of contact to bend a rod by moving pivotably coupled handles relative to one another. These devices, however, can be limited in their ability to achieve large bending forces or displacements due to their design.

Accordingly, there is a need for improved rod benders that address shortcomings of prior designs, e.g., to provide increased force on an implant to enable bending of implants formed from high-strength materials.

SUMMARY

The present disclosure provides for ratchet-style rod bender instruments and related methods that enable bending of implants, including implants made of materials that require greater bending force to shape than provided by conventional rod benders. Rod bender instruments disclosed herein can include two bending elements that can move symmetrically and simultaneously about a stationary support to bend a rod using three points of contact (e.g., in the fashion of a "French" rod bender) with movement of a single actuator handle of the rod bender. The rod bender can include a gear train having a plurality of compound gears that can be driven by a ratchet wheel using one or more movements of the actuator handle. Movement of the actuator handle relative to a housing of the rod bender can rotate the ratchet wheel, thereby driving the plurality of compound gears to move the bending elements and bend an implant received within an implant-receiving channel of the instrument. Further, the gear train can provide significant mechanical advantage and the ratchet wheel configuration can allow for multiple actuator handle movement cycles, thereby enabling greater rod bending force and displacement relative to conventional French-style rod bending tools.

In one aspect, an instrument for bending an implant is disclosed that includes a housing, a handle pivotably coupled to the housing, a gear train coupled to the housing, and an implant-receiving channel. A first bending element and a second bending element are coupled to the gear train. Movement of the handle relative to the housing drives symmetric movement of the first and second bending elements to bend an implant received within the implant-receiving channel.

The instruments and methods described herein can have a number of additional features and/or variations, all of which are within the scope of the present disclosure. For example, the instrument can further include a support structure coupled to the housing. The implant-receiving channel can be defined by the first bending element, the second bending element, and the support structure. Movement of the handle relative to the housing can drive symmetric movement of the first and second elements from a first position to a second position. The second position can be defined by a first mechanical stop configured to contact the first bending element and a second mechanical stop configured to contact the second bending element. The first bending element can be coupled to a first gear of the gear train and the second bending element can be coupled to a second gear of the gear train. At least one of the first gear and the second gear can include a mechanical stop, and movement of the handle relative to the housing can be configured to bring at least one of the first bending element and the second bending element into contact with the mechanical stop. In some embodiments, the second gear can include a first mechanical stop and the first gear can include a second mechanical stop, such that movement of the handle relative to the housing can bring the first bending element into contact with the second mechanical stop and the second bending element into contact with the first mechanical stop.

In some embodiments, movement of the handle relative to the housing can drive symmetric movement of the first and second bending elements along an arcuate path. The movement of the handle can drive the first bending element in a clockwise direction and the second bending element in a counterclockwise direction. A first end of the handle can be pivotably coupled to the housing. The implant-receiving channel can be perpendicular to a longitudinal axis of the housing. In some embodiments, movement of the handle relative to the housing can drive symmetric movement of the first and second bending elements from a first position to a second position, with the second position located distal to the first position. The gear train of the instrument can include at least two compound gears. In some embodiments, the gear train can provide a mechanical advantage greater than about 15.

In another aspect, an instrument for bending an implant includes a housing, a gear train coupled to the housing, a handle, and an implant-receiving channel. The gear train has a first compound gear, a second compound gear, and at least one gear wing. At least one bending element is coupled to the at least one gear wing. The handle is coupled to the housing to drive the gear train, and the implant-receiving channel is configured to receive an implant to be bent by the at least one bending element against one or more support elements.

As noted above, the instruments and methods described herein can have a number of additional features and/or variations, all of which are within the scope of the present disclosure. For example, the gear train can include a ratchet wheel engaged with the first compound gear. Movement of the handle can cause rotation of the ratchet wheel, which can drive rotation of the first compound gear and the second compound gear. In some embodiments, the ratchet wheel is a compound gear. The handle can include a driving pawl that can engage with the ratchet wheel. The instrument can further include a locking pawl that can engage with the ratchet wheel. The locking pawl can be located remote of the driving pawl.

The first compound gear can be engaged with the second compound gear and the at least one gear wing. In some such embodiments, a major gear of the first compound gear can be engaged with the second compound gear and a minor gear of the first compound gear can be engaged with the at least one gear wing. The at least one gear wing can include a first gear wing and a second gear wing. The at least one bending element can include a first bending element coupled to the first gear wing and a second bending element coupled to the second gear wing. The first gear wing can be engaged with the first compound gear and the second gear wing can be engaged with the second compound gear. Movement of the handle can drive the gear train to move the at least one bending element. In some embodiments, the gear train can provide a mechanical advantage greater than about 15.

In another aspect, a method includes placing an implant in an implant-receiving channel of an implant bending instrument and driving a compound gear train to symmetrically move a plurality of bending elements to intersect the implant-receiving channel and bend the implant received therein. Driving the compound gear train can include actuating a single handle to rotate a first compound gear of the compound gear train. The method can further include releasing the handle while the bending elements remain stationary. A second compound gear and a third compound gear of the compound gear train can drive a first gear wing and a second gear wing to symmetrically move the plurality of bending elements. The bending elements can move symmetrically relative to a support structure about which the implant is bent. In some embodiments, the method can further include releasing a locking pawl to drive the compound gear train in reverse and move the plurality of bending elements away from the implant-receiving channel.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure. Additionally, to the extent that linear or circular dimensions are used in the description of the disclosed devices and methods, such dimensions are not intended to limit the types of shapes that can be used in conjunction with such devices and methods. Equivalents to such linear and circular dimensions can be determined for different geometric shapes. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

Instruments and methods are disclosed herein for bending or contouring an implant, e.g., for use in a surgical procedure. Implant benders (also referred to herein as rod benders) of the present disclosure can include a plurality of bending elements that can be symmetrically driven by a compound gear train to bend or contour an implant. A single handle or lever can be actuated by a user, either manually or robotically assisted, to drive the gear train and move the plurality of bending elements symmetrically in a first direction. After a desired contour angle, i.e., a desired bend radius, of the implant is achieved, a locking pawl can be released to permit return of the bending elements to a starting position. Instruments of the present disclosure can impart a greater mechanical advantage and a greater displacement of the bending elements than conventional rod-benders. This can expand the range of implants that can be contoured using instruments and methods of the present disclosure to materials that have too high a yield strength for bending with conventional rod benders.

Figure 1:
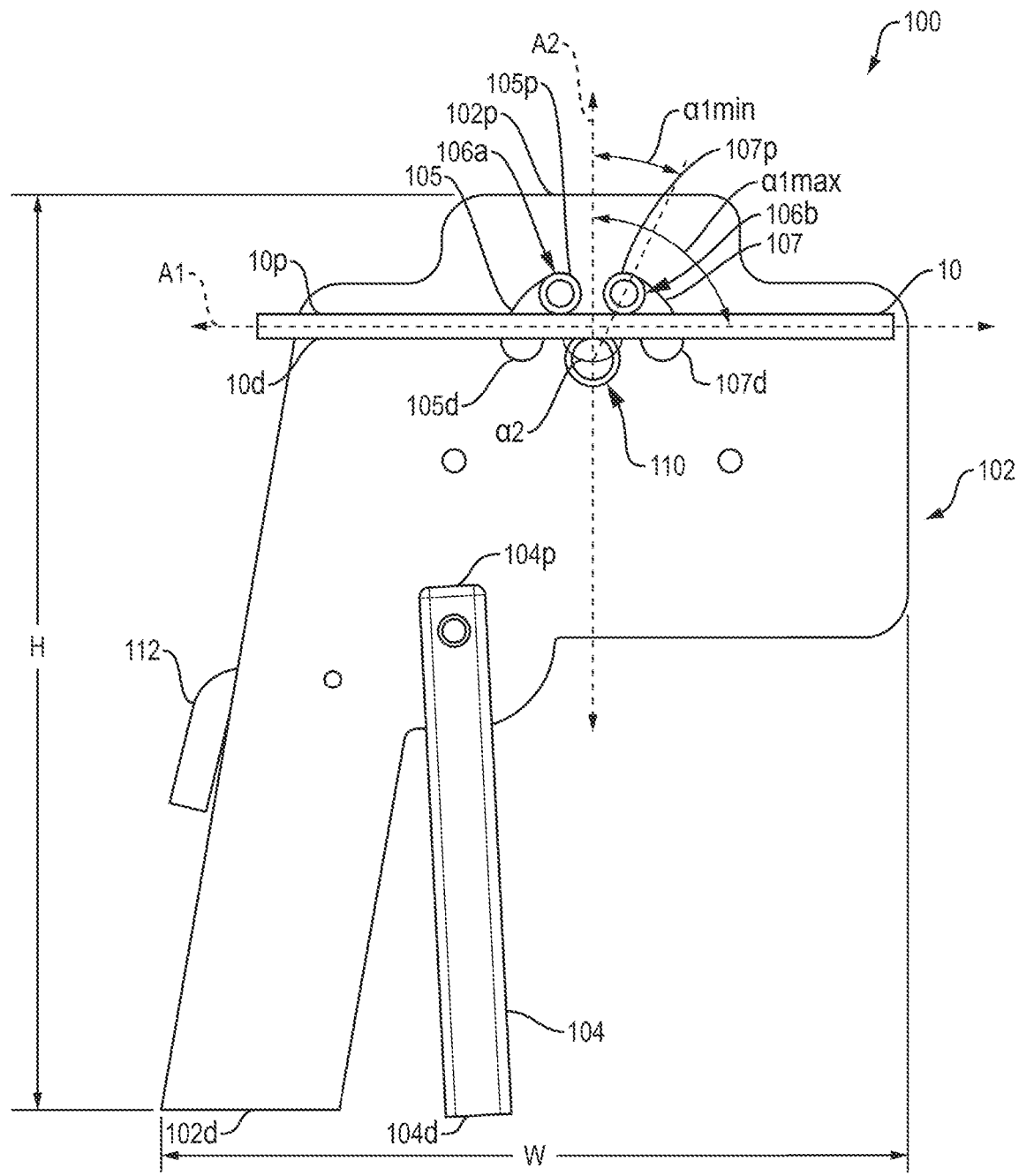
FIG. 1 is a front view of one embodiment of an implant bender instrument of the present disclosure with the bending elements of the instrument in a first position and an implant to be bent received within an implant-receiving channel of the instrument.
Figure 2:
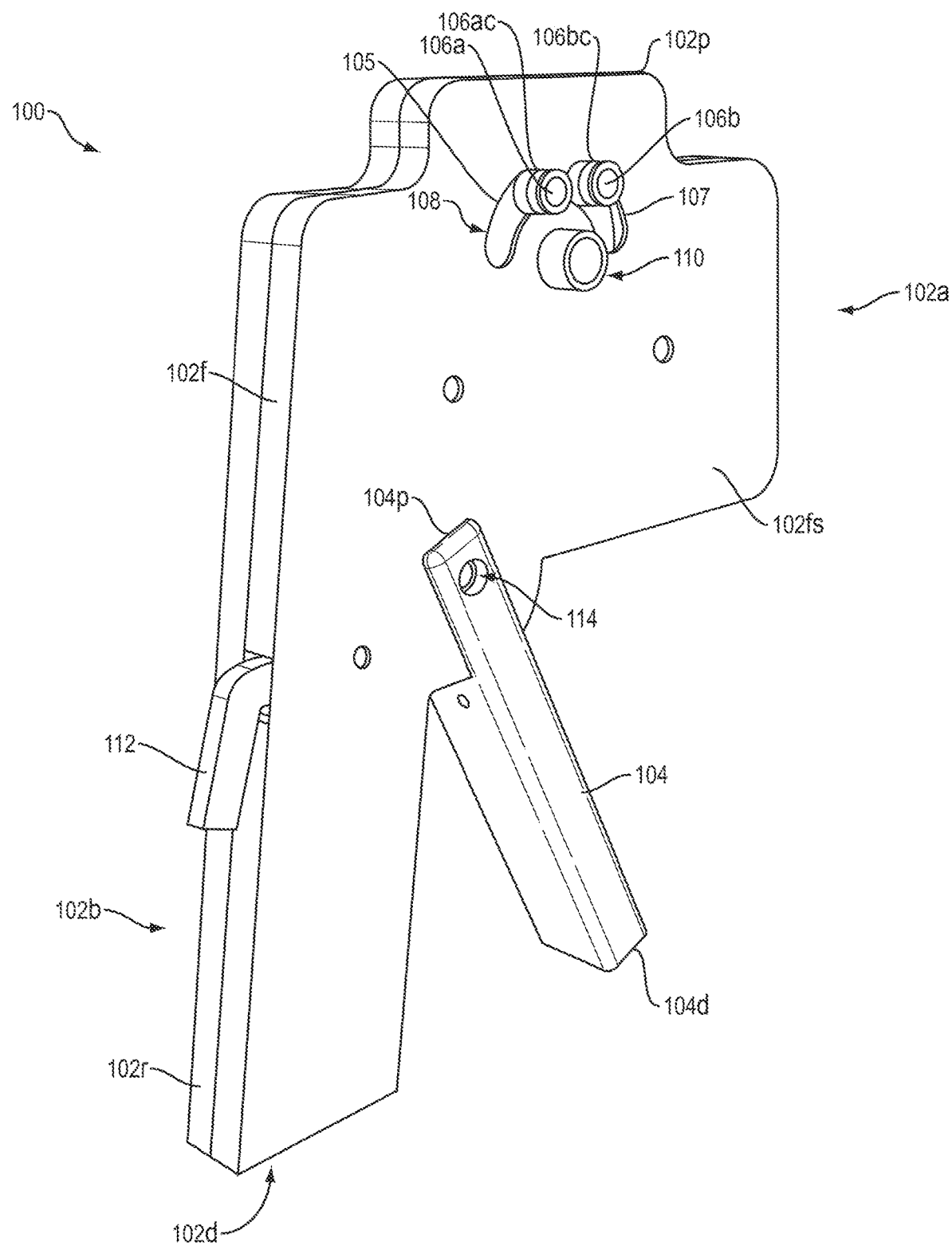
FIG. 2 is a perspective view of the implant bender instrument of FIG. 1.

FIGS. 1 and 2 illustrate one embodiment of a rod bender instrument 100 of the present disclosure having a housing 102, an actuator handle 104, and two bending elements 106a, 106b. The actuator handle 104 can drive a gear train 300 (see FIG. 4A) to move the first and second bending elements 106a, 106b to bend or contour a rod 10 or other implant received within an implant-receiving channel 108 (see FIG. 2) of the instrument 100. The bending elements 106a, 106b can extend through slots 105, 107 in the housing 102 and can move symmetrically across the implant-receiving channel 108. The implant-receiving channel 108 can be defined, at least in part, by the bending elements 106a, 106b and a support structure 110 such that an implant within the implant-receiving channel 108 can be held, at least in part, between the bending elements 106a, 106b and the support structure. In some embodiments, one or both of the bending elements 106a, 106b and/or the support structure 110 can include retention feature(s) that can, at least in part, retain the rod 10 or other implant within the implant-receiving channel 108. For example, in some embodiments one or both of the support structures 110 can include a cutout or notch 106ac, 106bc (see FIG. 2) that can engage with a surface of the rod 10 to hold the rod in place. Additionally, or alternatively, the support structure 110 can have an outer surface with a concave shape or complementary contour to the rod 10 or other implant received within the implant-receiving channel 108 that can retain the rod therein. As can be seen in FIG. 1, the bending elements 106a, 106b can contact the rod 10 received within the implant-receiving channel 108 on a first side 10p thereof, while the support structure 110 can contact the rod on a second side 10d opposite the first side. A longitudinal axis A1 of the implant-receiving channel 108 can extend substantially perpendicular to an axis of symmetry A2 that can extend through the support structure 110. The axis of symmetry A2 can define an axis about which the bending elements 106a, 106b move symmetrically to bend the rod 10. In some embodiments, the axis of symmetry A2 can extend along a proximal-distal axis of the housing 102, i.e., a longitudinal axis of the instrument 102, and the rod-receiving channel 108 can extend substantially perpendicular to the proximal-distal axis. The longitudinal axis of the housing 102 (also referred to as the proximal-distal axis of the housing) can extend from a first or proximal end 102p of the housing to a second or distal end 102d of the housing. The first or proximal portion 102p of the housing can be formed from a main body 102a of the housing and the second or distal end 102d of the housing can be formed from a gripping portion 102b of the housing. Construction of the housing 102 is discussed in further detail below.

FIG. 1 illustrates the bending elements 106a, 106b in a first or initial position, with the bending elements 106a, 106b located at a proximal end 105p, 107p of respective slots 105, 107. The actuator handle 104 can be moved to drive the gear train 300 (see FIG. 4A) to symmetrically move the bending elements 106a, 106b distally within the slots 105, 107. As described in detail below, a proximal end 104p of the actuator handle 104 can be pivotally coupled to the housing 102 such that a driving pawl 104p of the actuator handle is in contact with the gear train 300. Moving a distal end 104d of the actuator handle towards the housing 102 can cause the driving pawl 104p to rotate the gear train 300 and move the bending elements 106a, 106b symmetrically about the support structure 110. The bending elements 106a,106b can intersect the implant-receiving channel 108 with distal movement within the slots 105, 107 and exert a bending force on the rod 10 received within the implant-receiving channel 108. A locking pawl 112 can selectively prevent proximal movement of the bending elements 106a, 106b. The locking pawl 112 can extend through the housing 102 and can be released to permit proximal movement of the bending elements 106a, 106b, e.g., to return the bending elements to the first position.

The instrument 100 can have a mechanical advantage greater than about 20, greater than about 30, or greater than about 40. The mechanical advantage provided by instruments of the present disclosure can be up to at least 7 times greater than conventional implant-bending instruments, which can allow a user to bend an implant while exerting less force than previously required. Further, the bending displacement can be 2 times or more than conventional implant-bending instruments, which can allow a user to bend an implant to a greater degree or angle. Moreover, the implant bending instruments of the present disclosure can be used to bend or contour implants made from material with a strength too high to be bent using convention implant-bending instruments. Examples of such materials can include various Nickel-Cobalt alloys, Molybdenum Rhenium alloys, and Cobalt-Chromium alloys, though others are possible as well. As discussed in detail below, instruments of the present disclosure can be used to bend an implant to a contour angle α2 of between about 180° and about 40°. To achieve contouring of the implant 10, each of the bending elements 106a, 106b can move symmetrically along an arcuate path between a minimum bending angle α1 min and a maximum bending angle α1 max. As discussed in detail below, α1 min can correspond to a first or initial position of the bending elements 106a, 106 while α1 max can correspond to a second or final position of the bending elements 106a, 106b (see, for example, FIG. 10). In some embodiments, the angle α1 can range from about 10° to about 70°. In some embodiments, the implant bending instrument 100 can have a height H, measured from the proximal end 102p of the housing 102 to the distal end 102d of the housing, of about 415 mm and a width W, measured perpendicular to the H, of about 338 mm.

Turning to FIG. 2, the housing 102 can have a front panel 102f and a rear panel 102r with an interior space formed therebetween. A main body 102a of the housing 102 can hold the gear train 300 (see FIG. 4A) and provide attachment points for the bending elements 106a, 106b and support structure 110. The slots 105, 107 can be formed in the main body 102a of the front panel 102f of the housing 102 and, in some embodiments, can be formed towards a proximal end 102p of the housing 102. The bending elements 106a, 106b can extend through the slots 105, 107 such that the bending elements protrude from the front panel 102f of the housing. Similarly, the support structure 110 can extend through a bore 120 (see FIG. 3) formed in the front panel 102f. The implant-receiving channel 108 can be formed against a front face of the front panel 102f. A gripping portion 102b of the housing can extend distally from the main body 102a to form a stationary handle that can be used in combination with the movable actuator handle 104 in a trigger-like fashion. The actuator handle 104 can be pivotally connected to the housing 102 at a pivot point 114 such that the actuator handle 104 can pivot towards and away from the gripping portion 102b while the gripping portion remains stationary. In some embodiments, the pivot point 114 can be formed in a distal portion of the main body 102a. An opening 116 can be formed in the housing 102 through which a portion of the locking pawl 112 can extend to allow selective release of the locking pawl. In the illustrated embodiment of FIG. 2, the opening 116 is formed in the front panel 102f of the housing 102. Alternatively, the opening 116 can be formed, in whole or in part, in the rear panel 102r.

Figure 3:
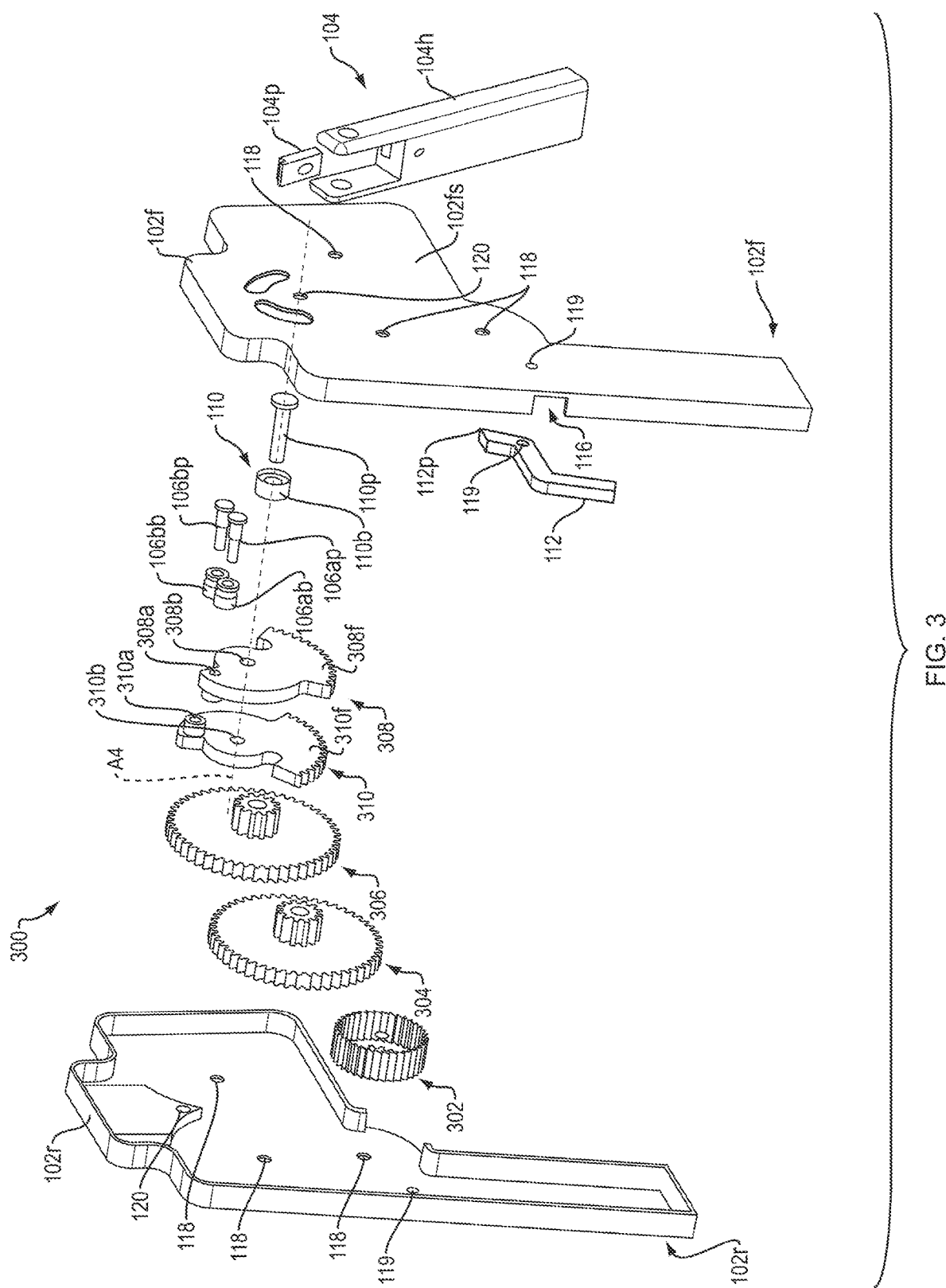
FIG. 3 is a perspective exploded view of the implant bender instrument of FIG. 1.

FIG. 3 is an exploded view of the instrument 100 of FIGS. 1 and 2, which makes visible components of the gear train 300 contained within the main portion 102a of the housing 102. The gear train 300 can include a plurality of compound gears 302, 304, 306, a first gear wing 308, and a second gear wing 310. The housing panels 102f, 102r can have bores 118 that can receive pins (not shown) to mount and retain the compound gears 302, 304, 306 within the housing 102. The actuator handle 104 can include a housing 104h and a driving pawl 104p that can extend proximally from the handle housing. The actuator handle 104 can be mounted to the housing 102 of the instrument 100 such that the driving pawl 104p contacts the first compound gear 302 (also referred to herein as the ratchet wheel) to rotate the first compound gear and drive the gear train 300. The pivot point 114 that pivotally couples the actuator handle 104 to the housing 102 can align with the mounting bore 118 for the ratchet wheel 302 such that the actuator handle is pivotally mounted about the center point of the gear.

Figure 4A:
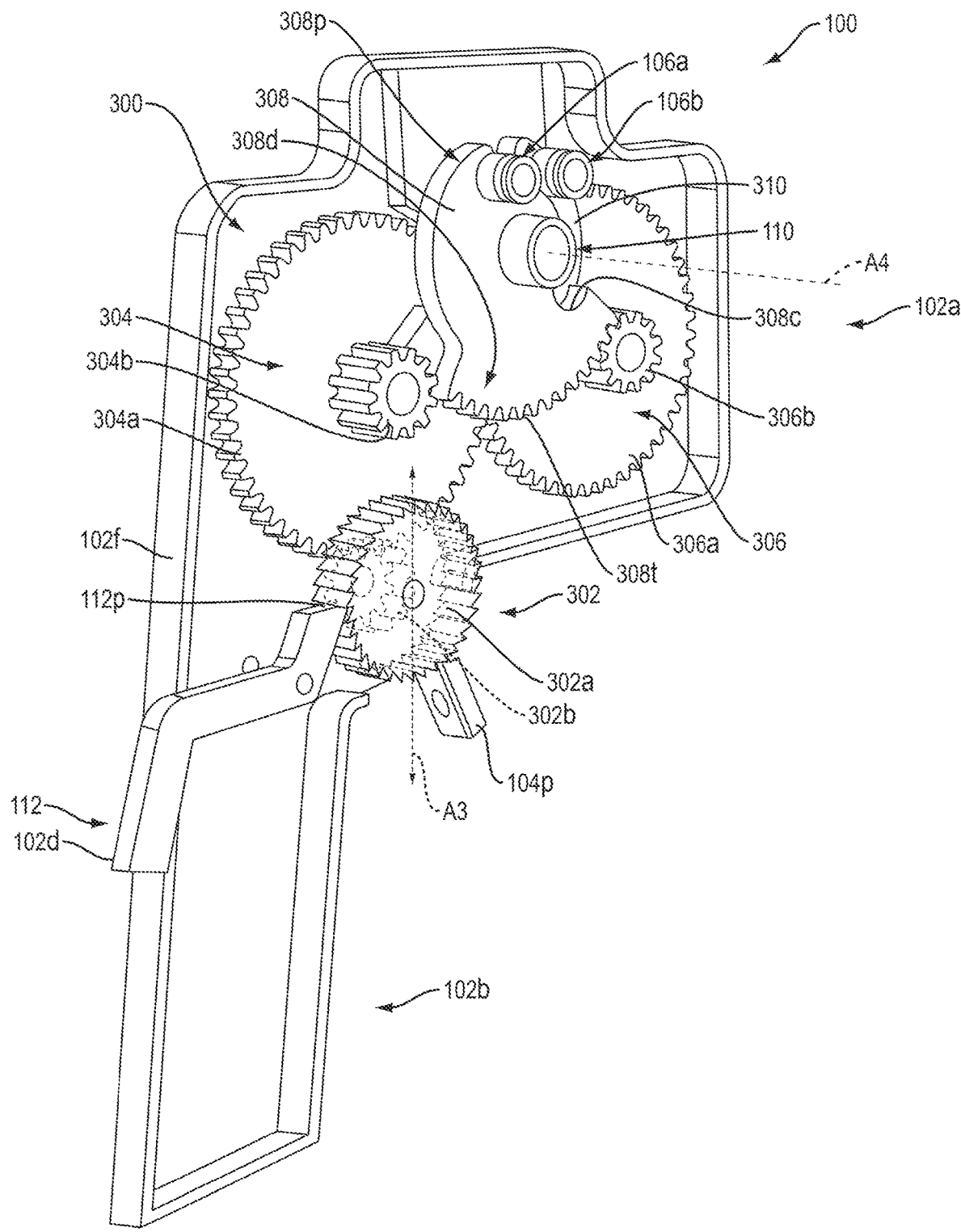
FIG. 4A is a front perspective view of the implant bender instrument of FIG. 1 with a front panel of a housing removed.

The locking pawl 112 can extend into the housing 102, e.g., through the opening 116 in the front panel 102f of the housing, such that a proximal end 112p of the locking pawl contacts the ratchet wheel 302 (see FIG. 4A). More particularly, the proximal end of the locking pawl 112p can contact a gear tooth of the ratchet wheel 302 (see FIG. 4A) and serve as a rotation stop to prevent unintended counter-rotation of the ratchet wheel 302, i.e., in a direction opposite the direction of rotation when the ratchet wheel 302 is driven by the actuator handle 104. Bores 119 can be formed in the front and rear panels of the housing 102f, 102r to receive a mounting pin (not shown) to hold the locking pawl 112 within the housing 102. A distal end 112d of the locking pawl 112 can act as a lever and extend outside the housing 102 to selectively release the locking pawl 112 and permit counter-rotation of the ratchet wheel 302. In this manner, the gear train 300 can be driven in reverse to move the bending elements 106a, 106b proximally within the respective slots 105, 107. As can be more clearly seen in FIGS. 4A and 4B, the locking pawl 112 and the driving pawl 104p can contact the ratchet gear 302 at remote locations, i.e., spaced apart from one another. For example, with the handle 104 in the initial or resting position, the locking pawl 112p can contact the ratchet gear 302 on a first side of a proximal-distal axis A3 that extends through the center point of the ratchet gear 302 while the driving pawl 104p can contact the ratchet gear 302 on a second side of the axis A3 opposite the first side.

The first and second bending elements 106a, 106b can be coupled to the first and second gear wings 308, 310, respectively. The bending elements 106a, 106b can each include a roller body 106ab, 106bb and a mounting pin 106ap, 106bp. The mounting pins 106ap, 106bp can extend through a lumen in the respective roller bodies 106ab, 106bb and through a first mounting bore 308a, 310a in the respective gear wings 308, 310, to couple the bending element thereto. The gear wings 308, 310 can also include a second bore 308b, 310b that can receive a mounting pin 110p of the support structure 110. More particularly, the mounting pin 110p of the support structure 110 can extend through a body 110b of the support structure, a mounting bore 120 in the front housing panel 102f, the second bores 308b, 310b of the first and second gear wings 308, 310, and a mounting bore 120 in the rear housing panel 102r. The body 110b of the support structure 110 can extend from the front panel 102f of the housing. In some embodiments, the mounting pin 110p can mount the support structure body 110b to the housing 102 such that a face of the support structure body 110b sits flush against the front housing panel 102f. The body 110b of the support structure 110 and the roller bodies 106ab, 106bb of the bending elements 106 can have a height suitable to retain an implant within the implant-receiving channel 108 formed between the bending elements 106a, 106b and the support structure 110 (see FIG. 2). The height of the bodies 110b, 106ab, 106bb can be measured as the distance that the support structure and bending elements 106ab, 106bb, respectively, extend perpendicular to a front surface 102fs of the front panel housing 102f.

Turning now to the gear wings 308, 310, the first gear wing 308 can have a proximal end 308p and a distal end 308d with a plurality of gear teeth 308t formed at the distal end. The first and second bores 308a, 308b can each be a through bore that extends from a front face 308f of the first gear wing 308 through a rear face 308r of the first gear wing (see FIG. 4B). The first bore 308a can be formed in the proximal end 308p of the first gear wing. The second bore 308b can be more centrally located on the first gear wing 308 than the first bore 308a. As discussed in detail below, the gear teeth 308t of the first gear wing 308 can engage with the third compound gear 306 of the gear train 300 to rotate the first gear wing about a rotation axis A4. The second gear wing 310 can have a proximal end 310p and a distal end 310d with a plurality of gear teeth 310t formed at the distal end. The first and second bores 310a, 310b can each be a through bore extending from a front face 310f of the second gear wing 310 through a rear face 310r of the gear wing (see FIG. 4B). The gear teeth 310t of the second gear wing 310 can engage with the second compound gear 304 of the gear train 300 to rotate the second gear wing 310 about the rotation axis A4. The first and second gear wings 308, 310 can be symmetrically mounted (see FIG. 5) such that the first and second gear wings mirror one another within the housing 102. Further, in some embodiments the first and second gear wings 308, 310 can be the same size, including pitch diameter of gear teeth 308t, 310t formed thereon, etc. As can best be seen in FIGS. 7 and 8, the first and second gear wings 308, 310 can be flush with one another such that at least a portion of the rear face 308r of the first gear wing 308 contacts a portion of the front face 310f of the second gear wing 310.

Figure 9:
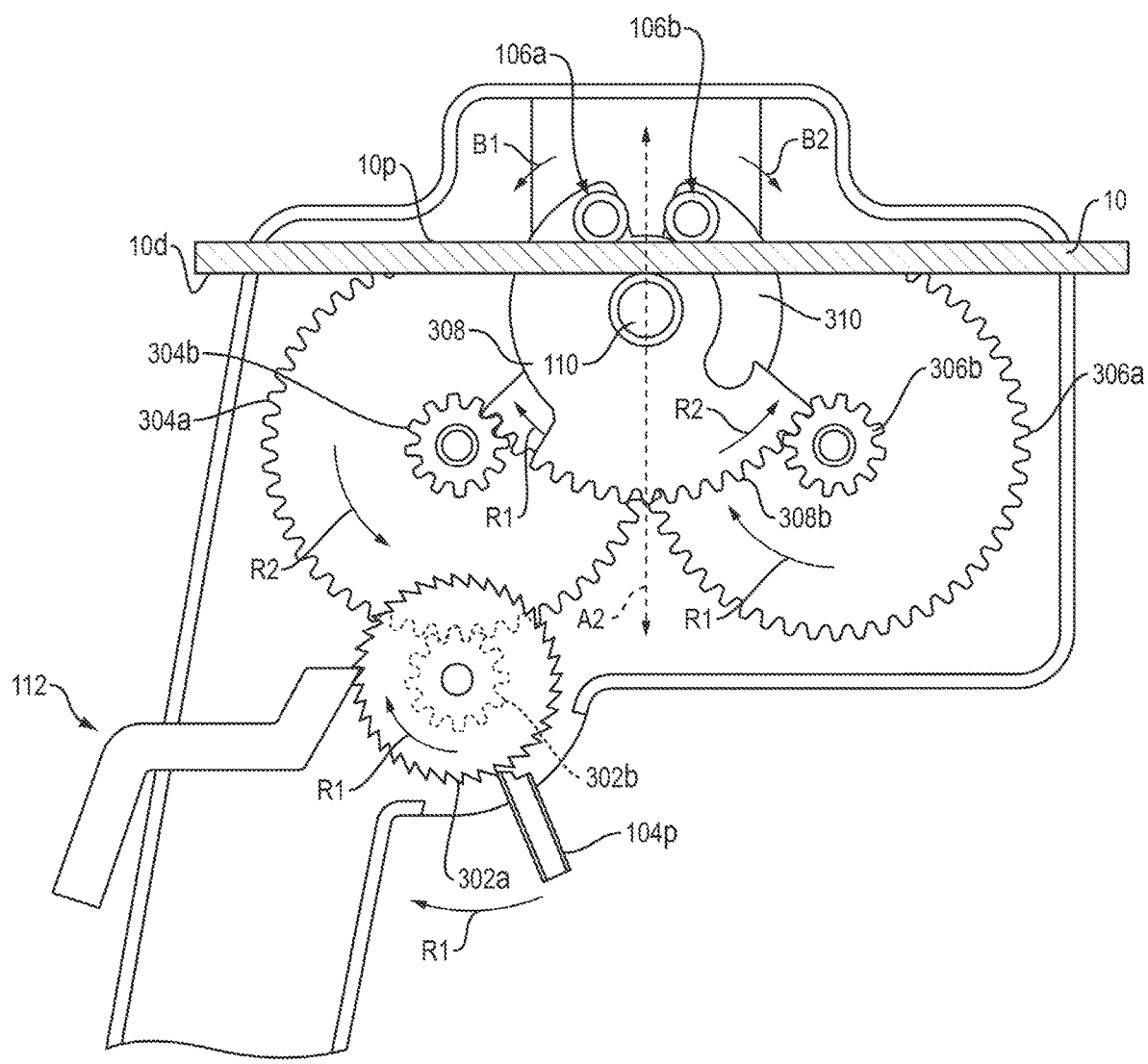
FIG. 9 is a front view of the implant bender instrument of FIG. 1 in an initial position with the front panel housing removed and an implant received within an implant-receiving channel.
Figure 10:
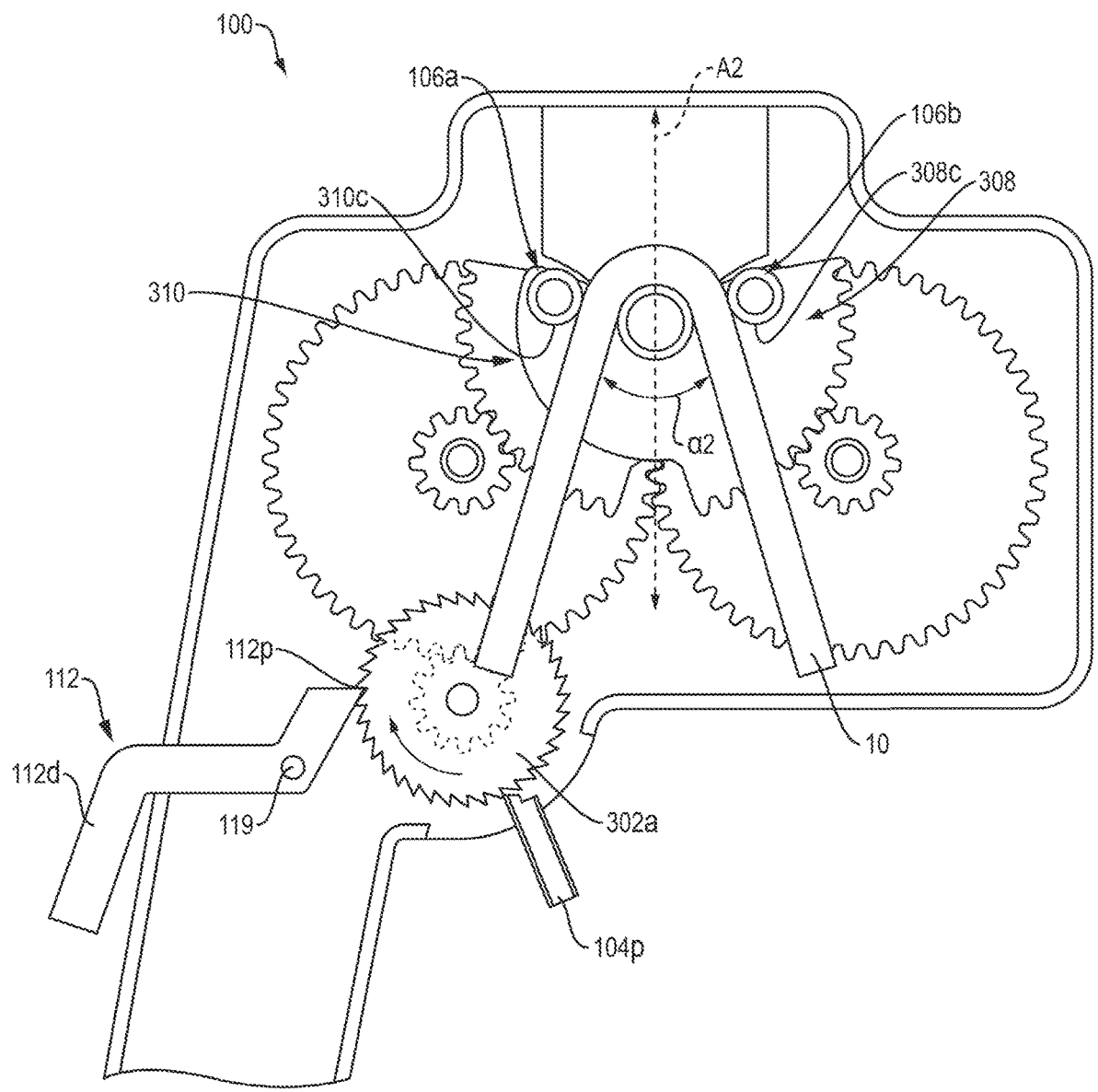
FIG. 10 is a front view of the implant bender instrument of FIG. 1 in a final position with the front panel housing removed and the implant received within the implant-receiving channel in a bent state.

As discussed in detail below, the first and second gear wings 308, 310 can be mounted within the housing 102 such that the second bores 308b, 310b of the wings are co-axial with one another. In some embodiments, the first and second gear wings 308, 310 can be symmetrically mounted relative to the axis of symmetry A2. The gear wings 308, 310 can rotate symmetrically about the rotation axis A4 that can extend co-axially along the longitudinal axes of the second bores 308b, 310b. Accordingly, the bending elements 106a, 106b coupled to the gear wings 308, 310, respectively, can rotate symmetrically about the rotation axis A4. Put another way, the bending elements 106a, 106b can move symmetrically about the support structure 110 as the mounting pin 110p extends through the second bores 308b, 310b of the wings. As can be seen in FIG. 2, the bending elements 106a, 106b can intersect the implant-receiving channel 108 as the bending elements rotate about the support structure 110 within the respective slots 105, 107. An example of this movement can also be seen by comparing FIGS. 1 and 9 versus 10, with FIGS. 1 and 9 showing the bending elements 106a, 106b in a first configuration that accepts a straight rod 10, and FIG. 10 showing the bending elements moved to intersect the channel 108 and thereby cause a bending of the rod 10 about the bending elements and the support structure 110. In this manner, the roller bodies 106ab, 106bb of the bending elements 106a, 106b can symmetrically bend or contour an implant received within the implant-receiving channel 108 about the support structure 110.

Figure 4B:
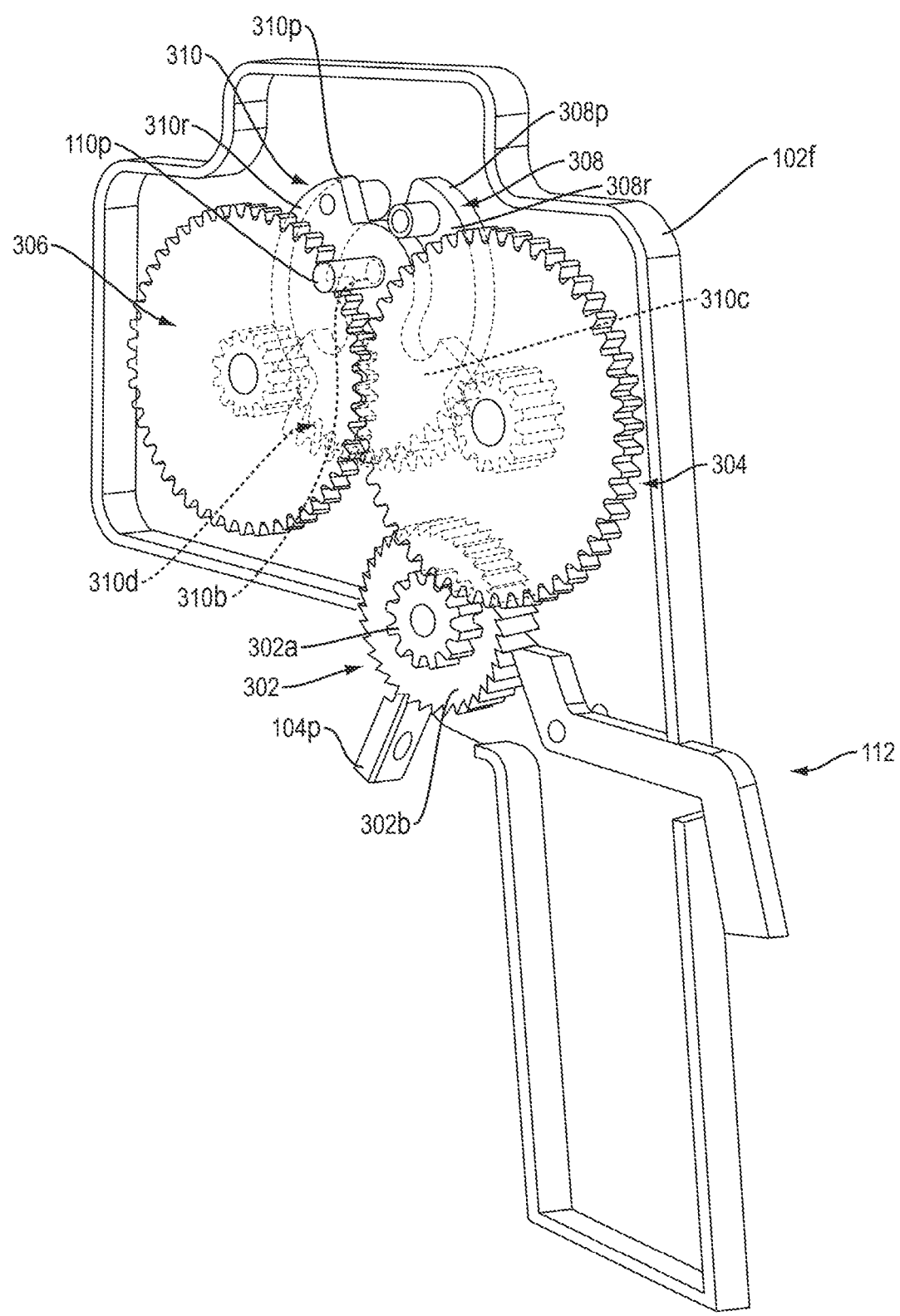
FIG. 4B is a rear perspective view of the implant bender instrument of FIG. 1 with a rear panel of the housing removed.
Figure 5:
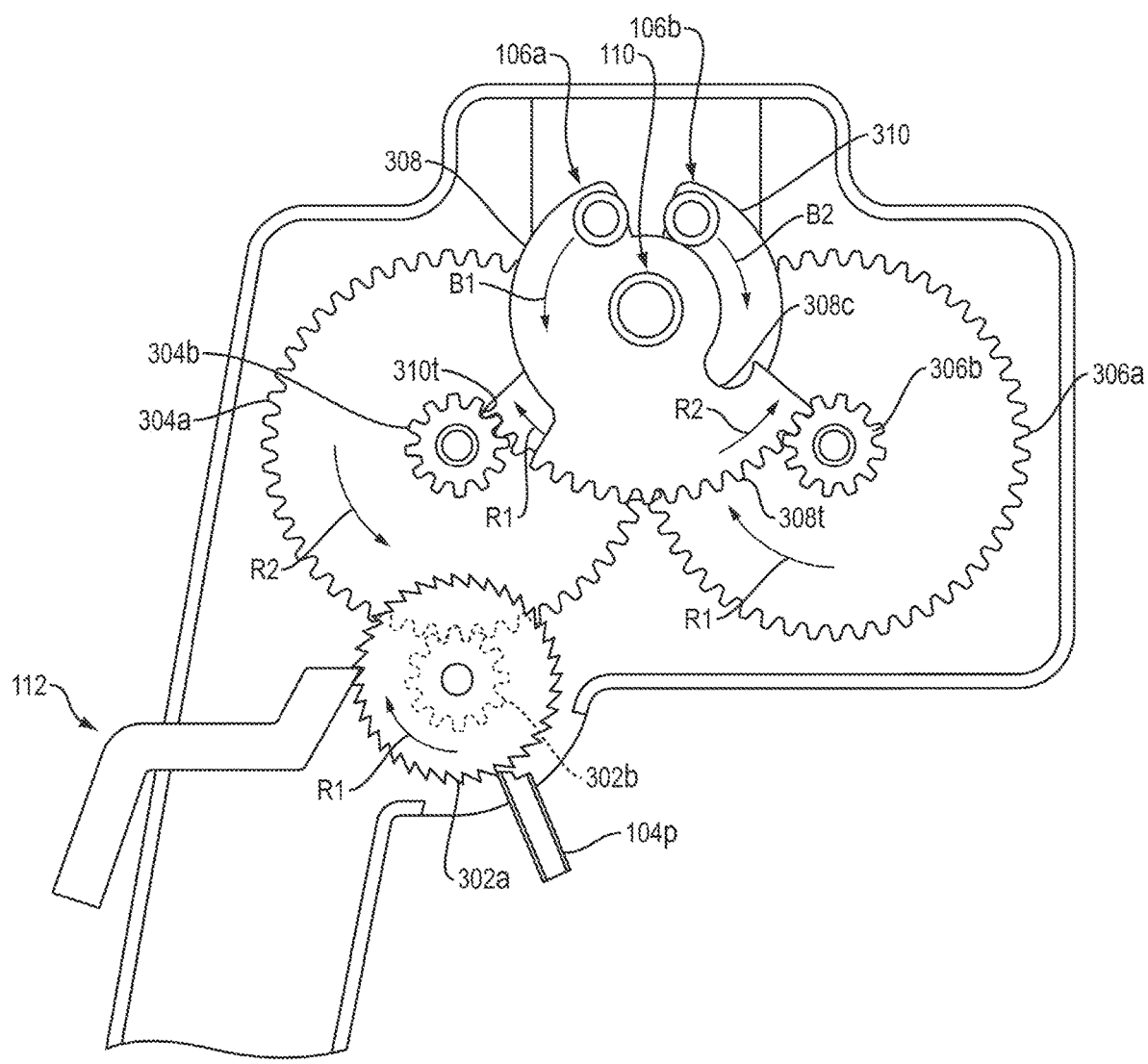
FIG. 5 is a front view of a portion of the implant bender instrument of FIG. 1 with the front panel housing removed and the bending elements in the first position.
Figure 6:
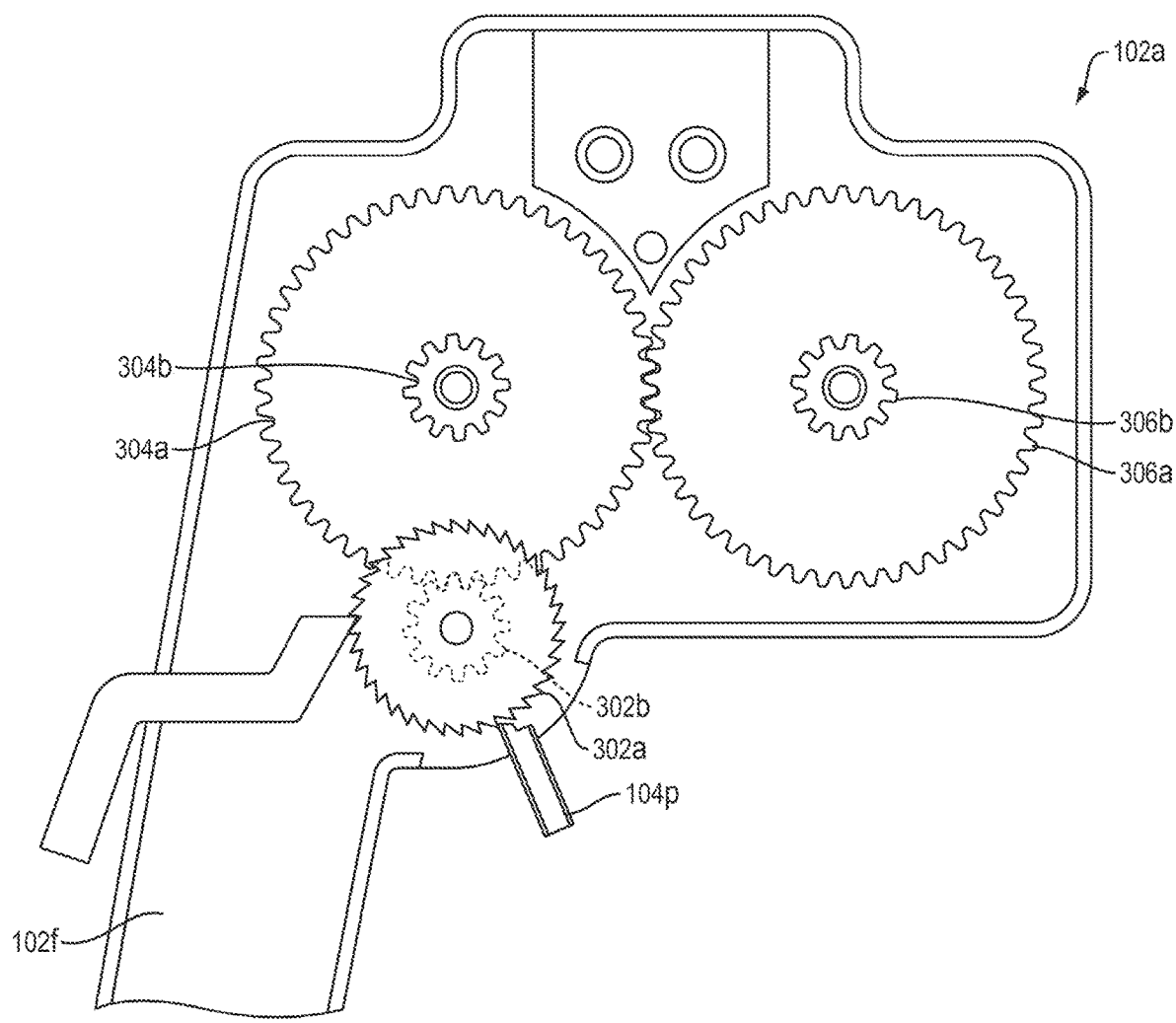
FIG. 6 is the front view of FIG. 5 with first and second gear wings hidden from view.
Figure 7:
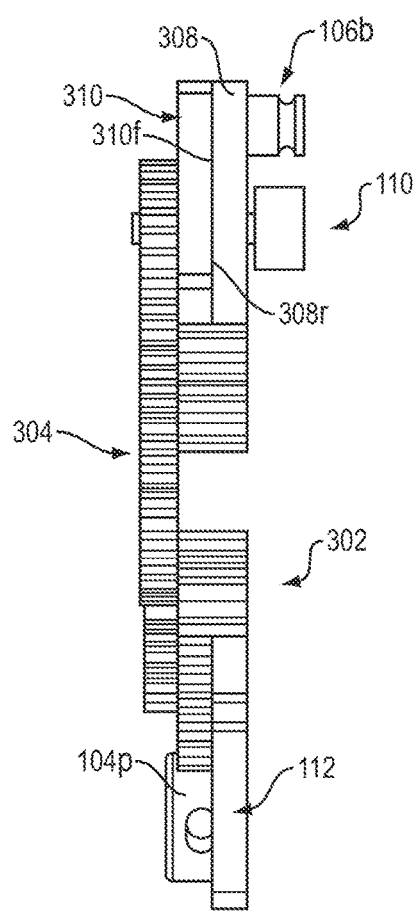
FIG. 7 is a side view of a gear train of the implant bender instrument of FIG. 1.
Figure 8:
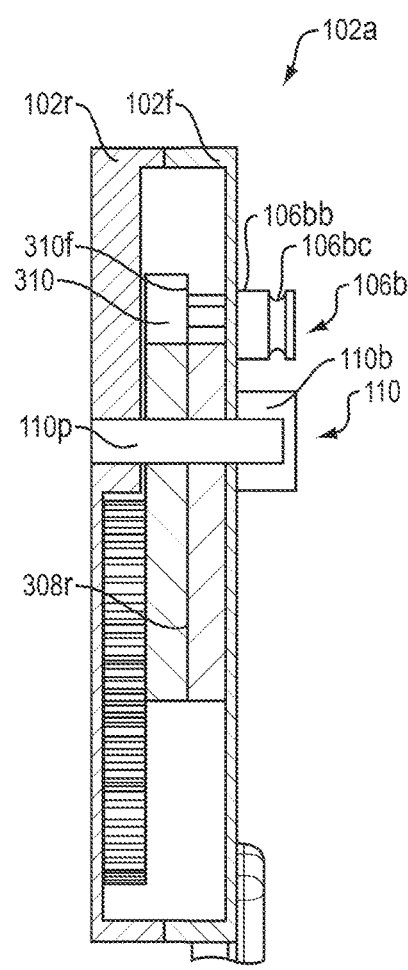
FIG. 8 is a side cross-sectional view of a main body portion of the implant bender instrument of FIG. 1 taken along the axis A2 in FIG. 1.

The gear train 300 will now be described in further detail with reference to FIGS. 4A-8. FIG. 4A is a front perspective view of the rod-bending instrument 100 of FIG. 1 with the front panel 102f of the housing 102 removed. FIG. 4B is a rear perspective view of the rod-bending instrument 100 of FIG. 1 with the rear panel 102r of the housing 102 removed. FIGS. 5 and 6 are front views of the main body portion 102a of the instrument 100 with the front panel 102f of the housing removed. FIG. 7 is a side view of the gear train 300 of the rod-bending instrument 100 of FIG. 1 and FIG. 8 is a side cross-sectional view of the main body portion 102a taken along the axis A2 from FIG. 1 (or, put another way, along a longitudinal axis of the mounting pin 110p of the support structure 110).

Each of the compound gears 302, 304, 306 can have a major gear 302a, 304a, 306a fixed to a minor gear 302b, 304b 306b such that the major gear and minor gear of a single compound gear rotate in the same direction and at the same speed. The driving pawl 104p of the actuator handle 104 can contact the major gear 302a of the first compound gear 302, the ratchet wheel, to drive the first compound gear 302 in a first direction R1. For ease of illustration, the housing 104h of the actuator handle 104 is not shown in FIGS. 3-5 such that the contact between the driving pawl 104p and the major gear 302a of the ratchet wheel 302 can be seen. Gear teeth of the minor gear 302b of the ratchet wheel 302 can mesh with gear teeth of the major gear 304a of the second compound gear 304 (also referred to herein as the first reducer gear). The minor gear 302b of the ratchet wheel can thus drive the major gear 304a of the first reducer gear 304 in a second direction R2 opposite the first direction R1. In the illustrated embodiment, the first direction R1 can be clockwise and the second direction R2 can be counterclockwise. In other embodiments, the first direction R1 can be counterclockwise and the second direction R2 can be clockwise. As can best be seen in FIG. 5, the major gear 304a of the first reducer gear 304 can mesh with the major gear 306a of the third compound gear 306 (also referred to herein as the second reducer gear) such that rotation of the major gear 304a of the first reducer gear 304 in the second direction R2 can drive rotation of the major gear 306a of the second reducer gear 306 in the first direction R1. Further, in some embodiments the first and second reducer gears 304, 306 can be identical, including pitch diameter of gear teeth, etc.

Turning now to the gear wings 308, 310, the first gear wing 308 can engage with the minor gear 306b of the second reducer gear 306 and the second gear wing 310 can engage with the minor gear 304b of the first reducer gear 304. The gear teeth 308t of the first gear wing 308 can mesh with the minor gear 306b of the second reducer gear 306 to rotate the first gear wing about the rotation axis A4. Accordingly, the bending element 106a coupled to the first gear wing 308 by the mounting pin 106ap can move along an arcuate path B1 with rotation of the first gear wing 308 about the rotation axis A4. The gear teeth 310t of the second gear wing 310 can mesh with the minor gear 304b of the first reducer gear 304 to rotate the second gear wing 310 about the rotation axis A4. Accordingly, the bending element 106b coupled to the second gear wing 310 by the mounting pin 106bp can move along an arcuate path B2 with rotation of the second gear wing 310 about the rotation axis A4.

As can be seen in FIGS. 4A, 4B, and 5, the first and second gear wings 308, 310 can be symmetrically mounted such that the first and second gear wings mirror one another within the housing 102 and the first and second bending elements 106a, 106b can move along symmetrical arcuate paths B1, B2. When mounted in the housing 102, the second bore 308b of the first gear wing 308 and the second bore 310b of the second gear wing 310 can be co-axial such that the mounting pin 110p of the support structure 110 extends through the second bore 308b, 310b of both the first and second gear wings 308, 310 (see FIGS. 7 and 8). Thus, the first and second gear wings, and the respective bending elements 106b, 106a coupled thereto, rotate about the common rotation axis A4 in a symmetrical manner. The minor gear 304b of the first reducer gear 304, which rotates in the second direction R2, can mesh with gear teeth 310t of the second gear wing 310 such that rotation of the minor gear 304b in the second direction can rotate the second gear wing 310 in the first direction R1. Similarly, the minor gear 306b of the second reducer gear 306, which rotates in the first direction R1, can mesh with gear teeth 308t of the first gear wing 308 such that rotation of the minor gear 306b in the first direction can rotate the first gear wing 308 in the second direction R2. The first and second bending elements 106a, 106b can travel along the symmetric arcuate paths B1, B2 in opposite directions from one another with the rotation of the first and second gear wings 308, 310.

The first gear wing 308 can include a cutout 308c that can serve as a mechanical stop for distal movement of the second bending element 106b. Likewise, the second gear wing 310 can include a cutout 310c (see FIG. 4B) that can serve as a mechanical stop for distal movement of the first bending element 106a. In the illustrated embodiment, the cutouts 308c, 310c can be U-shaped recesses that can mimic a rounded shape of the bending elements 106a, 106b such that the bending elements 106a, 106b can be received or seated within the respective cutouts 310c, 308c. More particularly, the distal end 308d (see FIG. 4A) of the first gear wing 308 and the distal end 310d (see FIG. 4B) of the second gear wing 310 can each move proximally along their respective rotational paths about the rotation axis A4 while the bending elements 106a, 106b coupled to the proximal ends 310p, 308p (see FIG. 4B) of the second and first gear wings 310, 308, respectively, move distally. The second bending element 106b coupled to the second gear wing 310 can move distally until movement of the second bending element is halted through contact with the cutout 308c of the first bending wing 308. Similarly, and simultaneously, the first bending element 106a coupled to the first gear wing 308 can move distally until movement of the first bending element is halted through contact with the cutout 310c of the second bending wing 310. The distal ends 105d, 107d of the slots 105, 107 can be formed in the front panel 102f to align with the mechanical stops 310c, 308c of the gear wings 310, 308 at the location where the bending elements 106a, 106b contact the mechanical stops. This location can be distal to or below the implant-receiving channel 108 and the distal side 10d of the rod 10 received within the implant-receiving channel 108 in an unbent or initial position, e.g., as shown in FIGS. 1 and 9. In this manner, movement of the bending elements 106a, 106b distally along the arcuate paths B1, B2 can exert a distal bending force on the rod 10, or other implant, received within the implant-receiving channel 108.

Operation of the rod bending instrument 100 will now be described with respect to FIGS. 9 and 10. FIG. 9 illustrates the rod-bending instrument 100 of FIG. 1 in the first or start position, with the bending elements 106a, 106b located at the proximal ends 105p, 107p of the slots 105, 107 and the rod 10 received within the implant-receiving channel 108 in an unbent or initial configuration, and the front housing panel 102*f* removed. FIG. 10 illustrates the rod-bending instrument 100 of FIG. 1 in the second or final position, with the bending elements 106*a*, 106*b* located at the distal ends 105*d*, 107*d* of the slots 105, 107 and the implant 10 contoured or bent accordingly, and the front housing panel 102*f* removed. In the initial position of FIG. 9, the implant 10 can be placed within the implant-receiving channel 108 such that the bending elements 106*a*, 106*b* are located on the first or proximal side 10*p* of the implant and the support structure 110 is located on the second or distal side of the implant. The bending elements 106*a*, 106*b* and support structure 110 can, at least in part, stabilize the implant 10 within the implant-receiving channel 108. The locking pawl 112 can be in its resting position, i.e., with the proximal end 112*p* of the locking pawl in contact with a gear tooth of the ratchet wheel 302. The actuator handle 104 and driving pawl 104*p* are also in the resting position, with the driving pawl 104*p* engaged with the ratchet wheel 302. In the illustrated embodiment, both the locking pawl 112 and the driving pawl 104*p* contact the major gear 302*a* of the ratchet wheel 302.

The actuator handle 104 can be moved toward the stationary handle portion of the housing such that the driving pawl 104*p* rotates the major gear 302*a* of the ratchet wheel 302 in the first direction R1 to drive the gear train 300. For example, a user can grip the housing of the handle 104*h* and depress the actuator handle 104 towards the grip portion of the housing 102*b*. The actuator handle 104 can thus rotate about the pivot point 114 in the first direction R1 which, in turn, can drive the major gear 302*a* of the ratchet wheel 302 in the first direction R1 as a result of the contact between the driving pawl 104*p* and the major gear 302*a*. The locking pawl 112 can permit rotation of the major gear 302*a* in the first direction R1. The major gear 302*a* can drive the gear train 300 as discussed above such that the first gear wing 308 rotates in the second direction R2 and the second gear wing 310 rotates in the first direction R1. This can move the first and second bending elements 106*a*, 106*b* from the first position towards the second position (see FIG. 10). More particularly, the bending elements 106*a*, 106*b* can move distally along symmetric arcuate paths B1, B2 (see FIG. 9) within the slots 105, 107. The bending elements 106*a*, 106*b* can be moved distally until each bending element contacts the mechanical stop 310*c*, 308*c* formed in the opposite gear wing 310, 308 and the bending elements 106*a*, 106*b* are located at the distal end 105*d*, 107*d* of the slots 105, 107 (see FIG. 10).

The rod 10 received within the implant-receiving channel 108 can be bent or contoured by the distal force exerted onto the rod 10 by the bending elements 106*a*, 106*b* as the bending elements 106*a*, 106*b* move distally along the arcuate path B1, B2. The support structure 110 can serve as a pivot point for bending of the rod 10 such that the rod can be bent inwards towards the axis of symmetry A2 that extends through the support structure 110. As noted above, the axis of symmetry A2 can extend perpendicular to the rod receiving channel 108.

Moving the bending elements 106*a*, 106*b* from the first position (see FIG. 9) to the second position (see FIG. 10) can require more than one actuation or depression of the actuator handle 104. In other words, a single depression of the actuator handle 104 can serve to move the bending elements 106*a*, 106*b* distally a partial length of the slots 105, 107. The actuator handle 104 can be released after a full depression. The actuator handle 104 can be biased such that, upon release, the actuator handle returns to the initial or resting position of FIG. 1. The locking pawl 112 can prevent counterrotation of the ratchet wheel 302 upon release and return of the actuator handle 104 to the initial position. Because the gear train 300 can remain stationary during release and return of the actuator handle 104, the bending elements 106*a*, 106*b* can hold their position within the slots 105, 107. Accordingly, upon a subsequent movement of the actuator handle 104, the bending elements 106*a*, 106*b* can continue distally along the arcuate path B1, B2 from an intermediate position within the slots 105, 107. This process can be repeated until a desired contour angle α2 of the rod 10 is achieved. A maximum contour angle α2 can be defined by the bending elements 106*a*, 106*b* in the final position, i.e., when the bending element s106*a*, 106*b* contact the respective mechanical stops 310*c*, 308*c* of the gear wings 310, 308 which prevent further rotation of the bending elements. In some embodiments, the maximum contour angle α2 can be between about 180° (at an initial position) and about 40° (at a final maximum bend position). A contour angle α2 less than the maximum contour angle can be achieved by driving the bending elements 106*a*, 106*b* to an intermediate position within the slots 105, 107 that is proximal to the distal end 105*d*, 107*d* of the slots, which can correspond to a position prior to contact between the bending elements 106*a*, 106*b* and the mechanical stops 310*c*, 308*c*.

Once the desired contour angle α2 is achieved, the rod 10 can be removed from the implant-receiving channel 108, e.g., by moving the rod 10 away from the front panel 102*f* of the housing, and the bending elements 106*a*, 106*b* can be moved proximally, e.g., returned to the initial position. As discussed above, in some embodiments, one or both of the bending elements 106*a*, 106*b* and/or the support structure 110 can have one or more retention features (see FIG. 2) that can at least partially retain the rod 10 within the implant-receiving channel 108. In some instances, the one or more retention features can prevent removal of the rod 10 from the implant-receiving channel 108 without first moving the bending elements 106*a*, 106*b* proximally to some extent. To this end, the locking pawl 112 can be released to permit counterrotation of the ratchet wheel 302, i.e., rotation of the ratchet wheel 302 in the second direction R2. The distal end 112*d* of the locking pawl 112 can be depressed towards the grip portion 102*b* of the housing 102. The locking pawl 112 can pivot about the pivot point 119 such that the proximal end 112*p* of the locking pawl comes out of engagement with the ratchet wheel 302, e.g., as a result of the proximal end 112*p* of the locking pawl moving about the pivot point 119 and out of contact with the gear tooth of the major gear 302*a* of the ratchet wheel. In some embodiments, the ratchet wheel 302 can be spring loaded or otherwise biased (e.g., using a coil or torsion spring around any of the various axes of rotation in the gear train) such that dis-engagement from the locking pawl 112 can cause the ratchet wheel to rotate in a direction opposite the direction of rotation by the driving pawl 104*p*. In other embodiments, one or more of the wings 310, 308 can be spring loaded or otherwise biased to achieve a similar effect. Counterrotation of the ratchet wheel 302 can drive the gear train 300 in reverse to move the bending elements 106*a*, 106*b* proximally along the arcuate path B1, B2 in the slots 105, 107. The bending elements 106*a*, 106*b* can be driven proximally by the gear train 300 until the bending elements contact the proximal end 105*p*, 107*p* of the respective slots 105, 107. At this point, the locking pawl 112 can be returned to the locking position, i.e., with the proximal end 112*p* of the locking pawl 112 engaged with the ratchet wheel 302 to prevent undesired movement of the bending elements.

The devices and methods disclosed herein can be used to bend or contour implants for use in minimally-invasive surgery and/or open surgery. While the devices and methods disclosed herein are generally described in the context of contouring a spinal rod for spinal surgery on a human patient, it will be appreciated that the methods and devices disclosed herein can be used to bend or contour implants for any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Reconditioning of a device can utilize a variety of techniques for disassembly, cleaning/replacement, and reassembly. Use of such techniques, and the resulting reconditioned device, are all within the scope of the present disclosure.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

Although specific embodiments are described above, changes may be made within the spirit and scope of the concepts described. Further features and advantages based on the above-described embodiments are also possible and within the scope of the present disclosure. Accordingly, the disclosure is not to be limited by what has been particularly shown and described. All publications and references cited herein are incorporated by reference in the entirety, except for any definitions, subject matter disclaimers or disavowals, and except to the extent that the incorporated material is inconsistent with the express disclosure herein, in which case the language in this disclosure controls.

Examples of the above-described embodiments can include the following:

1. An instrument for bending an implant, comprising:
    a housing;
    a handle pivotably coupled to the housing;
    a gear train coupled to the housing;
    a first bending element coupled to the gear train;
    a second bending element coupled to the gear train; and
    an implant-receiving channel;
    wherein movement of the handle relative to the housing drives symmetric movement of the first and second bending elements to bend an implant received in the implant-receiving channel.
2. The instrument of claim 1, further comprising a support structure coupled to the housing, wherein the implant-receiving channel is defined by the first bending element, the second bending element, and the support structure.
3. The instrument of claim 1 or 2, wherein movement of the handle relative to the housing drives symmetric movement of the first and second bending elements from a first position to a second position, the second position defined by a first mechanical stop configured to contact the first bending element and a second mechanical stop configured to contact the second bending element.
4. The instrument of any of claims 1 to 3, wherein the first bending element is coupled to a first gear of the gear train and the second bending element is coupled to a second gear of the gear train.
5. The instrument of claim 4, wherein at least one of the first gear and the second gear includes a mechanical stop; and wherein movement of the handle relative to the housing is configured to bring at least one of the first bending element and the second bending element into contact with the mechanical stop.
6. The instrument of any of claims 1 to 5, wherein movement of the handle relative to the housing drives symmetric movement of the first and second bending elements along an arcuate path.
7. The instrument of any of claims 1 to 6, wherein movement of the handle relative to the housing drives the first bending element in a clockwise direction and the second bending element in a counterclockwise direction.
8. The instrument of any of claims 1 to 7, wherein a first end of the handle is pivotably coupled to the housing.
9. The instrument of claim 8, wherein the implant-receiving channel is perpendicular to a longitudinal axis of the housing.
10. The instrument of claim 8 or 9, wherein movement of the handle relative to the housing drives symmetric movement of the first and second bending elements from a first position to a second position, the second position located distal to the first position.
11. The instrument of any of claims 1 to 10, wherein the gear train includes at least two compound gears.
12. The instrument of any of claims 1 to 11, wherein the gear train provides a mechanical advantage greater than about 15.
13. An instrument for bending an implant, comprising:
    a housing;
    a gear train coupled to the housing, the gear train having a first compound gear, a second compound gear, and at least one gear wing;
    at least one bending element coupled to the at least one gear wing;
    a handle coupled to the housing to drive the gear train; and
    an implant-receiving channel configured to receive an implant to be bent by the at least one bending element against one or more support elements.
14. The instrument of claim 13, wherein the gear train includes a ratchet wheel engaged with the first compound gear; and wherein movement of the handle causes rotation of the ratchet wheel, thereby driving rotation of the first compound gear and the second compound gear.

15. The instrument of claim 14, wherein the ratchet wheel is a compound gear.

16. The instrument of claim 14 or 15, wherein the handle includes a driving pawl engaged with the ratchet wheel.

17. The instrument of claim 16, further comprising a locking pawl engaged with the ratchet wheel, the locking pawl located remote of the driving pawl.

18. The instrument of any of claims 13 to 17, wherein the first compound gear is engaged with the second compound gear and the at least one gear wing.

19. The instrument of claim 18, wherein a major gear of the first compound gear is engaged with the second compound gear and a minor gear of the first compound gear is engaged with the at least one gear wing.

20. The instrument of any of claims 13 to 19, wherein movement of the handle drives the gear train to move the at least one bending element.

21. The instrument of any of claims 13 to 20, wherein the at least one gear wing includes a first gear wing and a second gear wing, and the at least one bending element includes a first bending element coupled to the first gear wing and a second bending element coupled to the second gear wing.

22. The instrument of claim 21, wherein the first gear wing is engaged with the second compound gear and the second gear wing is engaged with the first compound gear.

23. The instrument of any of claims 13 to 22, wherein the gear train provides a mechanical advantage greater than about 15.

24. A method, comprising:
    placing an implant in an implant-receiving channel of an implant bending instrument;
    driving a compound gear train to symmetrically move a plurality of bending elements to intersect the implant-receiving channel and bend the implant received therein.

25. The method of claim 24, wherein driving the compound gear includes actuating a single handle to rotate a first compound gear of the compound gear train.

26. The method of claim 25, further comprising releasing the handle while the bending elements remain stationary.

27. The method of any of claims 24 to 26, further comprising releasing a locking pawl to drive the compound gear train in reverse and move the plurality of bending elements away from the implant-receiving channel.

The invention claimed is:

1. An instrument for bending an implant, comprising:
   a housing;
   a handle pivotably coupled to the housing;
   a gear train coupled to the housing;
   a first bending element coupled to the gear train;
   a second bending element coupled to the gear train; and
   an implant-receiving channel;
   wherein movement of the handle relative to the housing drives symmetric movement of the first and second bending elements relative to the housing to bend an implant received in the implant-receiving channel.

2. The instrument of claim 1, further comprising a support structure coupled to the housing, wherein the implant-receiving channel is defined by the first bending element, the second bending element, and the support structure.

3. The instrument of claim 1, wherein movement of the handle relative to the housing drives symmetric movement of the first and second bending elements from a first position to a second position, the second position defined by a first mechanical stop configured to contact the first bending element and a second mechanical stop configured to contact the second bending element.

4. The instrument of claim 1, wherein the first bending element is coupled to a first gear of the gear train and the second bending element is coupled to a second gear of the gear train.

5. The instrument of claim 4, wherein at least one of the first gear and the second gear includes a mechanical stop; and
    wherein movement of the handle relative to the housing is configured to bring at least one of the first bending element and the second bending element into contact with the mechanical stop.

6. The instrument of claim 1, wherein movement of the handle relative to the housing drives symmetric movement of the first and second bending elements along an arcuate path.

7. The instrument of claim 1, wherein movement of the handle relative to the housing drives the first bending element in a clockwise direction and the second bending element in a counterclockwise direction.

8. The instrument of claim 1, wherein a first end of the handle is pivotably coupled to the housing.

9. The instrument of claim 8, wherein the implant-receiving channel is perpendicular to a longitudinal axis of the housing.

10. The instrument of claim 8, wherein movement of the handle relative to the housing drives symmetric movement of the first and second bending elements from a first position to a second position, the second position located distal to the first position.

11. The instrument of claim 1, wherein the gear train includes at least two compound gears.

12. The instrument of claim 1, wherein the gear train provides a mechanical advantage greater than about 15.

13. An instrument for bending an implant, comprising:
    a housing;
    a gear train coupled to the housing, the gear train having a first compound gear, a second compound gear, and at least one gear wing;
    at least one bending element coupled to the at least one gear wing;
    a handle coupled to the housing to drive the gear train; and
    an implant-receiving channel configured to receive an implant to be bent by the at least one bending element against one or more support elements.

14. The instrument of claim 13, wherein the gear train includes a ratchet wheel engaged with the first compound gear; and
    wherein movement of the handle causes rotation of the ratchet wheel, thereby driving rotation of the first compound gear and the second compound gear.

15. The instrument of claim 14, wherein the ratchet wheel is a compound gear.

16. The instrument of claim 14, wherein the handle includes a driving pawl engaged with the ratchet wheel.

17. The instrument of claim 16, further comprising a locking pawl engaged with the ratchet wheel, the locking pawl located remote of the driving pawl.

18. The instrument of claim 13, wherein the first compound gear is engaged with the second compound gear and the at least one gear wing.

19. The instrument of claim 18, wherein a major gear of the first compound gear is engaged with the second compound gear and a minor gear of the first compound gear is engaged with the at least one gear wing.

20. The instrument of claim 13, wherein movement of the handle drives the gear train to move the at least one bending element.

21. The instrument of claim 13, wherein the at least one gear wing includes a first gear wing and a second gear wing, and the at least one bending element includes a first bending element coupled to the first gear wing and a second bending element coupled to the second gear wing.

22. The instrument of claim 21, wherein the first gear wing is engaged with the second compound gear and the second gear wing is engaged with the first compound gear.

23. The instrument of claim 13, wherein the gear train provides a mechanical advantage greater than about 15.

* * * * *